(12) United States Patent
Rhim et al.

(10) Patent No.: US 8,547,799 B2
(45) Date of Patent: Oct. 1, 2013

(54) ULTRASONIC PROBE, ULTRASONIC IMAGING APPARATUS AND FABRICATING METHOD THEREOF

(75) Inventors: Sung Min Rhim, Incheon (KR); Ho Jung, Seoul (KR)

(73) Assignee: Humanscan Co., Ltd., Asan (KR)

( * ) Notice: Subject to any disclaimer, the term of this patent is extended or adjusted under 35 U.S.C. 154(b) by 832 days.

(21) Appl. No.: 12/699,166

(22) Filed: Feb. 3, 2010

(65) Prior Publication Data
US 2010/0204583 A1 Aug. 12, 2010

(30) Foreign Application Priority Data
Feb. 10, 2009 (KR) .......................... 10-2009-0010661

(51) Int. Cl.
*H04R 17/00* (2006.01)
(52) U.S. Cl.
USPC .......................................... 367/155

(58) Field of Classification Search
USPC ................. 310/334, 322, 326, 327, 311, 336; 128/66.23; 600/437, 659, 447; 367/173, 367/174, 140, 162, 155
See application file for complete search history.

(56) References Cited

U.S. PATENT DOCUMENTS

| 5,598,051 A * | 1/1997 | Frey .............................. 310/334 |
| 2004/0100163 A1* | 5/2004 | Baumgartner et al. ....... 310/334 |

* cited by examiner

*Primary Examiner* — Elmer Chao
(74) *Attorney, Agent, or Firm* — Stein IP, LLC

(57) ABSTRACT

An ultrasonic probe, an ultrasonic imaging apparatus and a fabricating method thereof are provided. The ultrasonic probe includes a rear block, a flexible printed circuit board having wiring patterns formed thereon, a piezoelectric wafer, a ground electrode plate, an acoustic matching layer, an acoustic lens, and a plurality of slots. Holes are formed in at least one of the rear block, the piezoelectric wafer and the acoustic matching layer and wiring patterns are formed in the form of a matrix array, and thus vibration property and focusing can be improved to obtain clear images.

12 Claims, 14 Drawing Sheets

ULTRASONIC PROBE, ULTRASONIC IMAGING APPARATUS AND FABRICATING METHOD THEREOF

CROSS-REFERENCE TO RELATED APPLICATIONS

This application claims the benefit of Korean Patent Application No. 10-2009-0010661, filed on Feb. 10, 2009, in the Korean Intellectual Property Office, the disclosure of which is incorporated herein by reference.

BACKGROUND OF THE INVENTION

1. Field of the Invention

The present invention relates to an ultrasonic probe, an ultrasonic imaging apparatus and a fabricating method thereof, and more particularly, to an ultrasonic probe, an ultrasonic imaging apparatus and a fabricating method thereof for enhancing vibration property and improving focusing of ultrasonic images to obtain clear images.

2. Description of the Related Art

Ultrasound is a method of examining tissues of the human body using ultrasonic waves, which irradiates ultrasonic waves to an affected area of the human body and detects an abnormal tissue through an image generated from a reflected signal. The ultrasound is used to diagnose lesions such as a tumor or test embryos.

Ultrasonic waves are defined as sound having a frequency higher than a frequency range that people can hear, generally, 20,000 Hz to 30 MHz. Ultrasonic waves for diagnosis of the human body are in the range of 1 MHz to 20 MHz.

An ultrasonic imaging apparatus used for ultrasound may be divided into three parts, that is, an ultrasonic probe, a signal processor and a display. The ultrasonic probe converts electric and ultrasonic signals and the signal processor processes receiving signals and transmitting signals. The display generates images using signals obtained from the ultrasonic probe and the signal processor. Particularly, the ultrasonic probe is an important part that determines the quality of an ultrasonic image.

The ultrasonic probe includes a piezoelectric wafer, an electrode, an acoustic matching layer, a printed circuit board and an acoustic lens, in general. The size of the ultrasonic probe is decreasing, which requires a method of arranging wiring patterns for processing ultrasonic and electric signals in the ultrasonic probe and a technique for improving vibration property and focusing to obtain clear ultrasonic images and widen a signal bandwidth.

SUMMARY OF THE INVENTION

The present invention provides an ultrasonic probe, an ultrasonic imaging apparatus and a fabricating method thereof for enhancing the vibration property of the ultrasonic imaging apparatus an improving focusing of ultrasonic images to obtain clear images.

According to an aspect of the present invention, there is provided an ultrasonic probe including a rear block having a predetermined thickness, a flexible printed circuit board stacked on the rear block to surround the top face and side of the rear block and having wiring patterns formed thereon, a-piezoelectric wafer stacked on the top face of the flexible printed circuit board and having upper and lower electrodes respectively formed on both sides thereof and a plurality of first vertical holes formed therein, a ground electrode plate stacked on the top face of the piezoelectric wafer, bonded to the upper electrode and connected to a ground layer of the flexible printed circuit board, an acoustic matching layer stacked on the top face of the ground electrode plate, an acoustic lens bonded onto the acoustic matching layer, and a plurality of slots formed in the direction perpendicular to the first vertical holes and ranging from in the acoustic matching layer to the top of the rear block.

The flexible printed circuit board includes a base film formed of an insulating material and having a bottom face bonded onto the rear block and a top face opposite to the bottom face, and wiring patterns formed on both sides of the base film. The wiring patterns includes a central wiring pattern that is formed on the top face of the base film, has a central pad formed between neighboring first vertical holes, is connected to the central pad through a via and is extended to the outside of the rear block through the bottom face of the base film, a first wiring pattern that has a first pad formed at one side of the central pad, is connected to the first pad and is arranged at one side of the top face of the base film, a second wiring pattern that has second pad formed on the other side of the central pad, is connected to the second pad and is arranged at the other side of the top face of the base film, a protective layer formed on the bottom face of the central wiring pattern and the top faces of the first and second wiring patterns to protect the central wiring pattern, the first and second wiring patterns, and a ground layer formed on the protective layer formed on the top faces of the first and second wiring patterns and connected to the ground electrode plate.

According to another aspect of the present invention, there is provided an ultrasonic imaging apparatus includes the ultrasonic probe and a main body having a connector connected to the ultrasonic probe.

According to another aspect of the present invention, there is provided a method of fabricating an ultrasonic probe, which includes a first stacking step of sequentially stacking a piezoelectric wafer, a ground electrode plate and an acoustic matching layer, a second hole forming step of forming a plurality of first vertical holes in the piezoelectric wafer, a second stacking step of sequentially stacking a rear block and a flexible printed circuit board, a third stacking step of stacking the piezoelectric wafer on the flexible printed circuit board, a slot forming step of forming a plurality of slots perpendicular to the first vertical holes such that the slots range from the acoustic matching layer to the top of the rear block, and a bonding step of bonding an acoustic lens onto the acoustic matching layer.

According to the present invention, holes are formed in at least one of the rear block, the piezoelectric wafer and the acoustic matching layer and a plurality of slots are formed through a one-time dicing process such that the slots range from the acoustic matching layer to the top of the rear block to form a wiring patterns in the form of a matrix array. Accordingly, the vibration property and focusing can be improved to obtain clear images.

Furthermore, the present invention reduces ultrasonic signal interference and provides a wide bandwidth and high sensitivity.

Moreover, a wiring pattern is arranged in the form of a matrix array to control ultrasonic signals or power used for ultrasound, and thus it is possible to adjust a focusing depth, extend an ultrasound area and obtain clear images.

In addition, the connector that connects the ultrasonic probe to the main body of the ultrasonic imaging apparatus is located on the top of the main body, and thus users can use the ultrasonic imaging apparatus conveniently.

Additional aspects and/or advantages of the invention will be set forth in part in the description which follows and, in part, will be obvious from the description, or may be learned by practice of the invention.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE EMBODIMENTS

Figure 1:
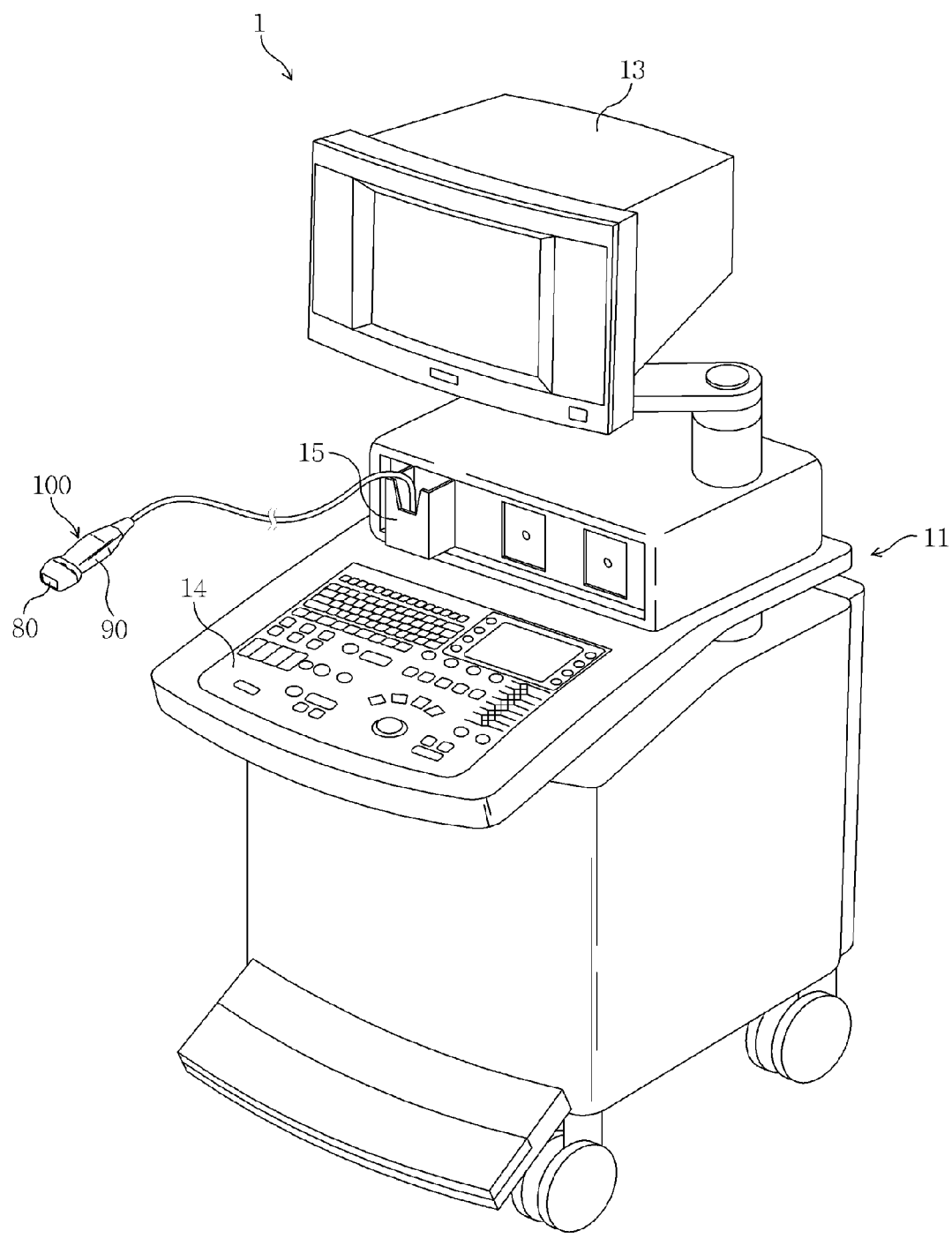
FIG. 1 illustrates an ultrasonic imaging apparatus according to a first embodiment of the present invention.

The present invention will now be described more fully with reference to the accompanying drawings, in which exemplary embodiments of the invention are shown. The invention may, however, be embodied in many different forms and should not be construed as being limited to the embodiments set forth herein; rather, these embodiments are provided so that this disclosure will be thorough and complete, and will fully convey the concept of the invention to those skilled in the art. Throughout the drawings, like reference numerals refer to like elements.

FIG. 1 shows an ultrasonic imaging apparatus 10 according to a first embodiment of the present invention. Referring to FIG. 1, the ultrasonic imaging apparatus 1 includes a main body 11, an ultrasonic probe 100, a display 13 and an input unit 14.

The main body 11 includes a signal processor that transmits and receives electric and ultrasonic signals and a storage unit that stores application programs and data required for ultrasound. Further, a connector 15 for connecting the ultrasonic probe 100 to the main body 11 is provided outside the main body 11. The connector 15 is placed on the top of the main body 11 such that a user can easily connect the ultrasonic probe 100 to the main body 11.

The ultrasonic probe 100 includes an acoustic lens 80 coming into contact with an affected area of a patient and a case 90 covering the other components of the ultrasonic probe 100. The acoustic lens 80 is used for focusing an ultrasonic image and arranged to cover an acoustic matching layer placed under the acoustic lens 80. The acoustic lens 80 may be made of silicon. The other components of the ultrasonic probe 100, covered with the case 90, will be explained in detail later.

The display 13 displays ultrasonic images obtained through application programs executed for ultrasound and examination.

The input unit 14 is used to execute the application programs or input data required for examination and includes a plurality of keys.

Figure 2A:
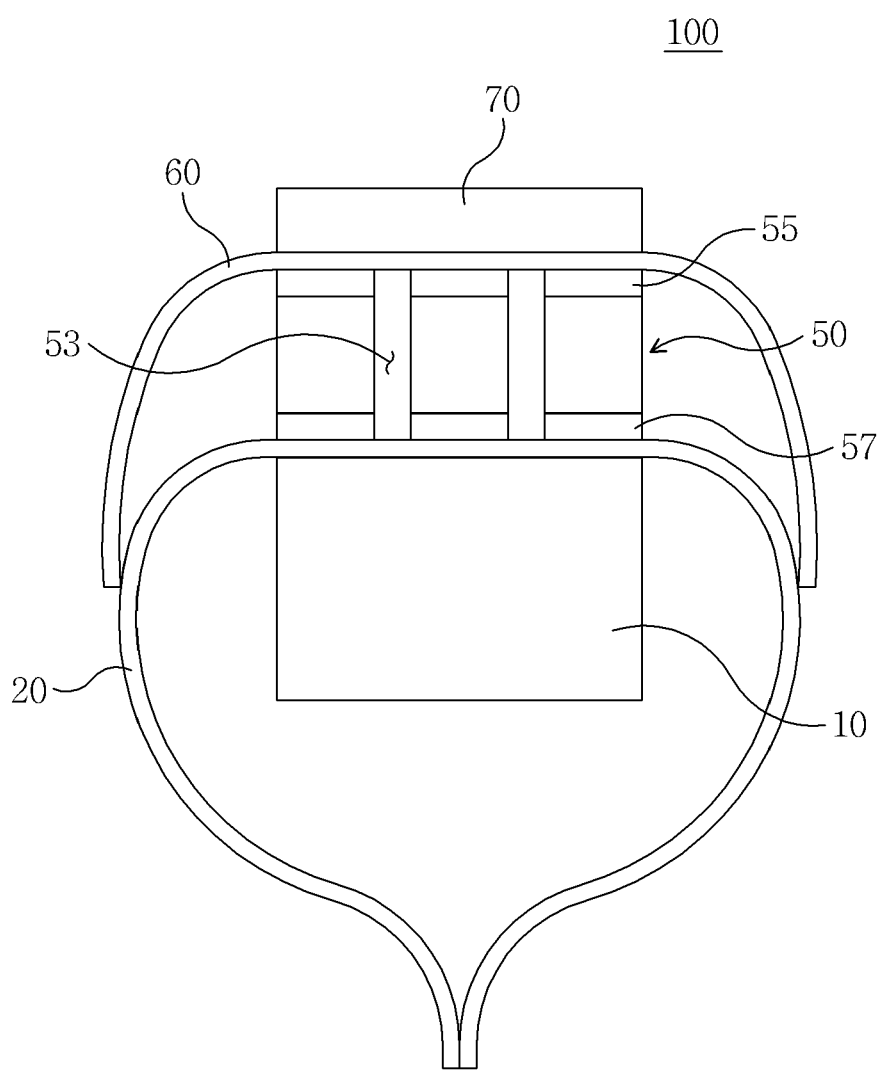
FIG. 2A is a cross-sectional view of an ultrasonic probe according to the first embodiment of the present invention.
Figure 2B:
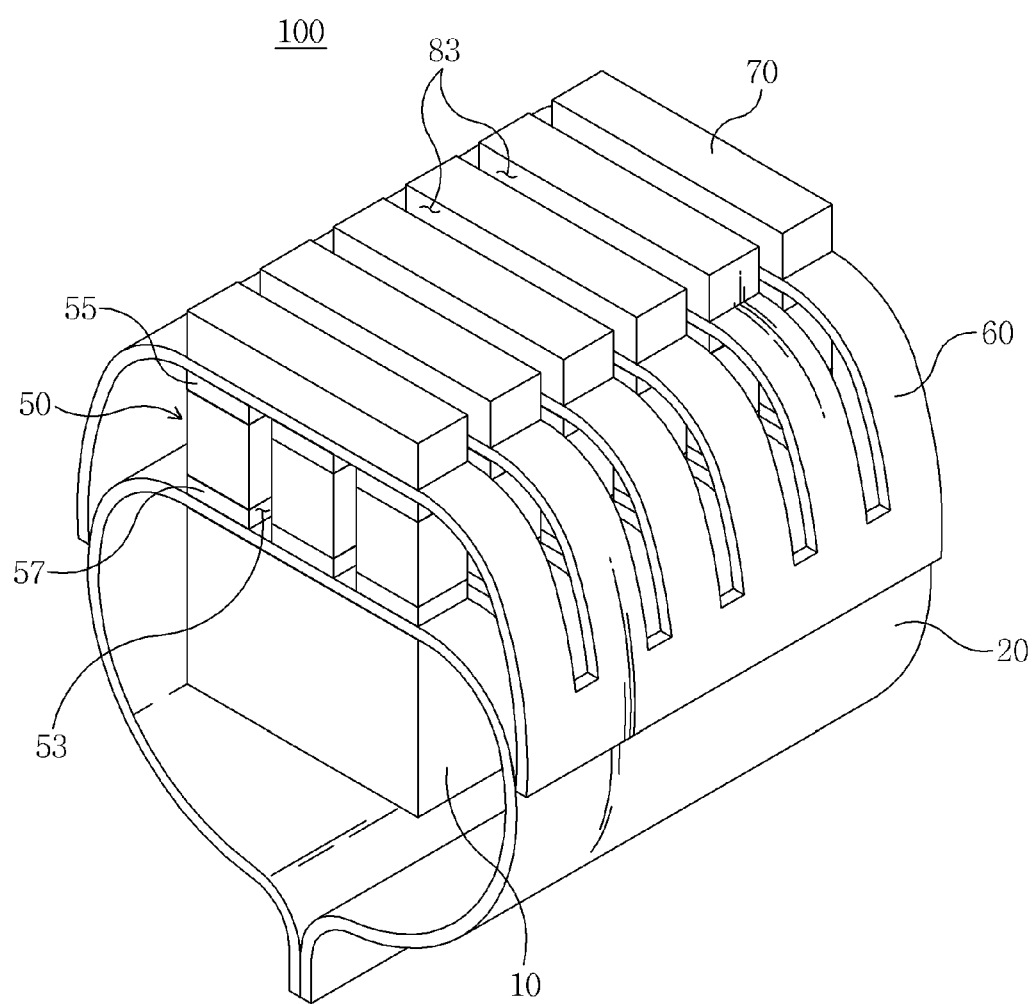
FIG. 2B: is a perspective view of the ultrasonic probe according to the first embodiment of the present invention.

The ultrasonic probe 100 according to the first embodiment of the present invention will now be explained with reference to FIGS. 2A and 2B. FIG. 2A is a cross-sectional view of the ultrasonic probe 100 according to the first embodiment of the present invention and FIG. 2B is a perspective view of the ultrasonic probe 100 according to the first embodiment of the present invention.

The ultrasonic probe 100 according to the first embodiment of the present invention includes a rear block 10, a flexible printed circuit board 20, a piezoelectric wafer 50, a ground electrode plate 60 and an acoustic matching layer 70, which are sequentially stacked. While the ultrasonic probe 100 according to the first embodiment of the present invention includes the acoustic lens 80 (shown in FIG. 1) placed on the acoustic matching layer 70, the acoustic lens is not shown in FIGS. 2A and 2B.

The rear block 10 is located at the bottom of the ultrasonic probe 100 and absorbs unnecessary ultrasonic signals traveling to the rear block 10 from the piezoelectric wafer 50.

The flexible printed circuit board 20 is located on the top face of the rear block 10 and has wiring patterns formed on both sides thereof. The flexible printed circuit board 20 will be explained in more detail later.

The piezoelectric wafer 50 is arranged on the top face of the flexible printed circuit board 20 and has upper and lower electrodes 55 and 57 respectively formed on both sides thereof and a plurality of first vertical holes 53.

While two first vertical holes 53 are formed in the piezoelectric wafer 50 in the first embodiment of the present invention, the number of first vertical holes is not limited thereto. The piezoelectric wafer 50 may be formed of PZT or PMN-PT. The upper and lower electrodes 55 and 57 are formed through sputtering, electron beam, thermal evaporation or electroplating. The upper electrode 55 is connected to the ground electrode plate 60 and the lower electrode 57 is connected to the flexible printed circuit board 20.

The ground electrode plate 60 has a metal layer formed on the top face thereof and an insulating layer formed on the bottom face thereof and surrounds the top face and the side of the piezoelectric wafer 50. The flexible printed circuit board 20 includes a ground layer. The bottom end of the ground electrode plate 60 is connected to the ground layer of the flexible printed circuit board 20.

The acoustic matching layer 70 is made of metal powder or ceramic powder and formed on the top face of the ground electrode plate 60.

A plurality of slots 83 are formed such that the plurality of slots 83 range from the acoustic matching-layer 70 to the top of the rear block 10 in the direction perpendicular to the first vertical holes 53. While the ultrasonic probe 100 according to the first embodiment of the present invention has five slots 83, the number of slots 83 is not limited thereto.

The acoustic lens (not shown) is used for focusing ultrasonic images and located on the top face of the acoustic matching layer 70.

Figure 3:
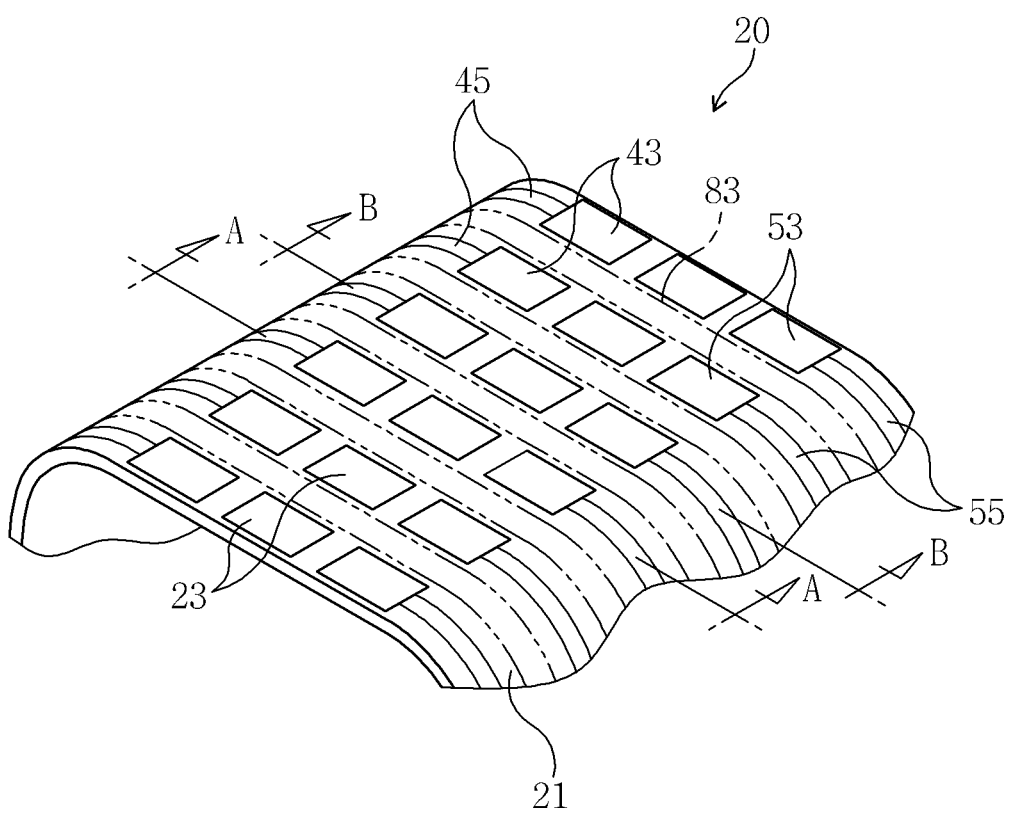
FIG. 3 is a perspective view of a flexible printed circuit board according to an embodiment of the present invention.
Figure 4A:
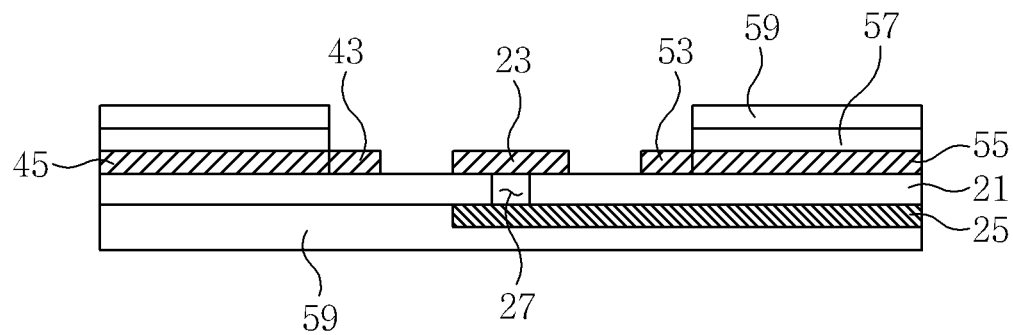
FIG. 4A is a cross-sectional view taken along line A-A of FIG. 3.
Figure 4B:
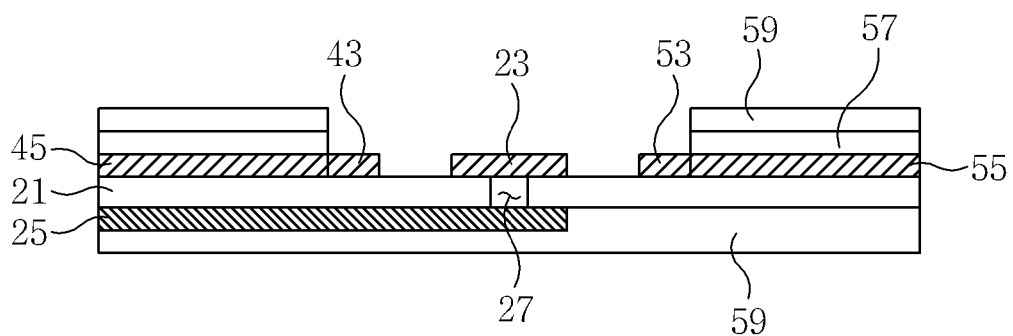
FIG. 4B is a cross-sectional view taken along line B-B of FIG. 3.

The flexible printed circuit board 20 and the wiring patterns according to the first embodiment of the present invention will now be explained with reference to FIGS. 2A, 2B, 3, 4A and 4B. FIG. 3 is a perspective view of the flexible printed circuit 20, FIG. 4A is a cross-sectional view taken along line A-A of FIG. 3 and FIG. 4B is a cross-sectional view taken along line B-B of FIG. 3.

FIG. 3 shows the flexible printed circuit board 20 before the slots 83 are formed. Positions of the slots 83 are indicated by dotted lines in FIG. 3.

The flexible printed circuit board 20 includes a base film 31 and wiring patterns. The base film 31 is made of an insulating material. The bottom face of the base film 31 is bonded to the top face of the rear block 10 and the top face thereof is opposite to the bottom face. The wiring patterns are divided into a central wiring pattern 33, a first wiring pattern 35 and a second wiring pattern 37 and formed on both sides of the base film 31.

The central wiring pattern 33 is formed on the top face of the base film 31 and includes a central pad 43 formed in the region between neighboring first vertical holes 53. The central wiring pattern 33 is connected to the central pad 43 through a via 39 and extended to the outside of the rear block 10 through the bottom face of the base film 31. Here, the central wiring pattern 33 is alternately arranged on one side and the other side of the central pad 43. Accordingly, the central wiring pattern 33 shown in FIG. 4A is located at the right side of the central pad 43 while the central wiring pattern 33 shown in FIG. 4B is formed at the left side of the central pad 43.

The first wiring pattern 35 includes a first pad 45 formed at one side of the central pad 43, is connected to the first pad 45 and arranged at one side of the top face of the base film 31. The second wiring pad 37 includes a second pad 47 formed at the other side of the central pad 43, is connected to the second pad 47 and arranged at the other side of the top face of the base film 31.

A protective layer 41 for protecting the wiring patterns is formed on the bottom face of the central wiring pattern 33 and the top faces of the first and second wiring patterns 35 and 37. Here, the central pad 43, the first pad 45 and the second pad 47 are not protected by the protective layer 41 and they are exposed to be connected to the lower electrode 57 of the piezoelectric wafer 50.

A ground layer 49 is formed on the protective layer 41 formed on the first and second wiring patterns 35 and 37 and connected to the ground electrode plate 60.

While the central pad 43, the first pad 45 and the second pad 47 form a 3.times.6 matrix array in the flexible printed circuit board 20 according to the first embodiment of the present invention, they can form 3.times.64 through 3.times.192 matrix arrays.

Furthermore, while the flexible printed circuit board 20 according to the first embodiment of the present invention has the three wiring patterns including the central wiring pattern 33, the first wiring pattern 35 and the second wiring pattern 37, the number of wiring patterns is not limited thereto. If five wiring patterns are formed, the central wiring pattern is alternately formed on one side and the other side of the bottom face of the base film, two wiring patterns are formed on one side of the central wiring pattern and the other two wiring patterns are formed on the other side of the central wiring pattern. The two wiring patterns are respectively arranged at both ends of the flexible printed circuit board.

In general, circuit connection is achieved at a contact portion of the piezoelectric wafer 50 and the flexible printed circuit board 20. A 1.5D (Dimension) ultrasonic probe has a multi-level circuit structure in order to connect circuits on both ends of the ultrasonic probe. However, the vibration and acoustic properties of the ultrasonic probe 100 increases as the thicknesses of the rear block 10, the piezoelectric wafer 50 and the acoustic matching layer 70, the flexible printed circuit 20 and the ground electrode plate 60 decreases. Accordingly, circuits on both sides of the flexible printed circuit board 20 according to the present invention are not connected at the contact portion of the flexible printed circuit board 20 and the piezoelectric wafer 50 and both ends of the flexible printed circuit board 20 are bonded to each other, as shown in FIG. 2B, and thus the thickness of the flexible printed circuit board 20 coming into contact with the piezoelectric wafer 50 decreases to improve the acoustic property of the ultrasonic probe 100.

Figure 5:
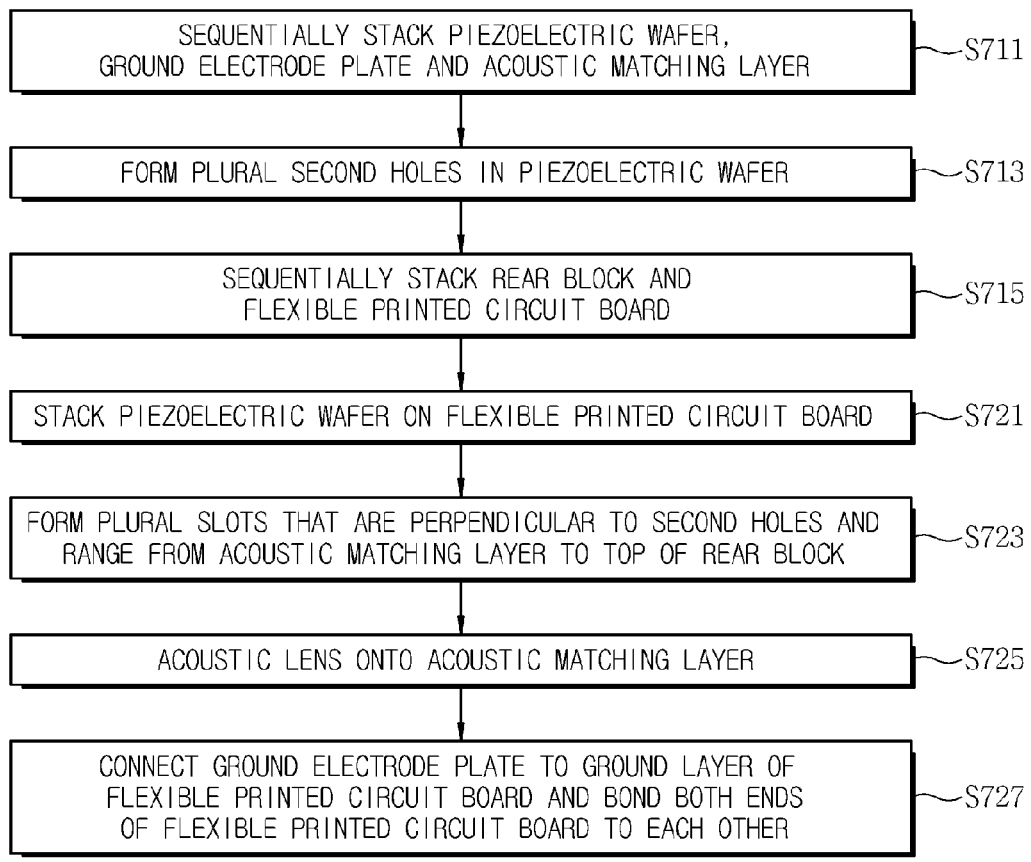
FIG. 5 is a flowchart showing a method of fabricating the ultrasonic probe according to the first embodiment of the present invention.
Figure 6:
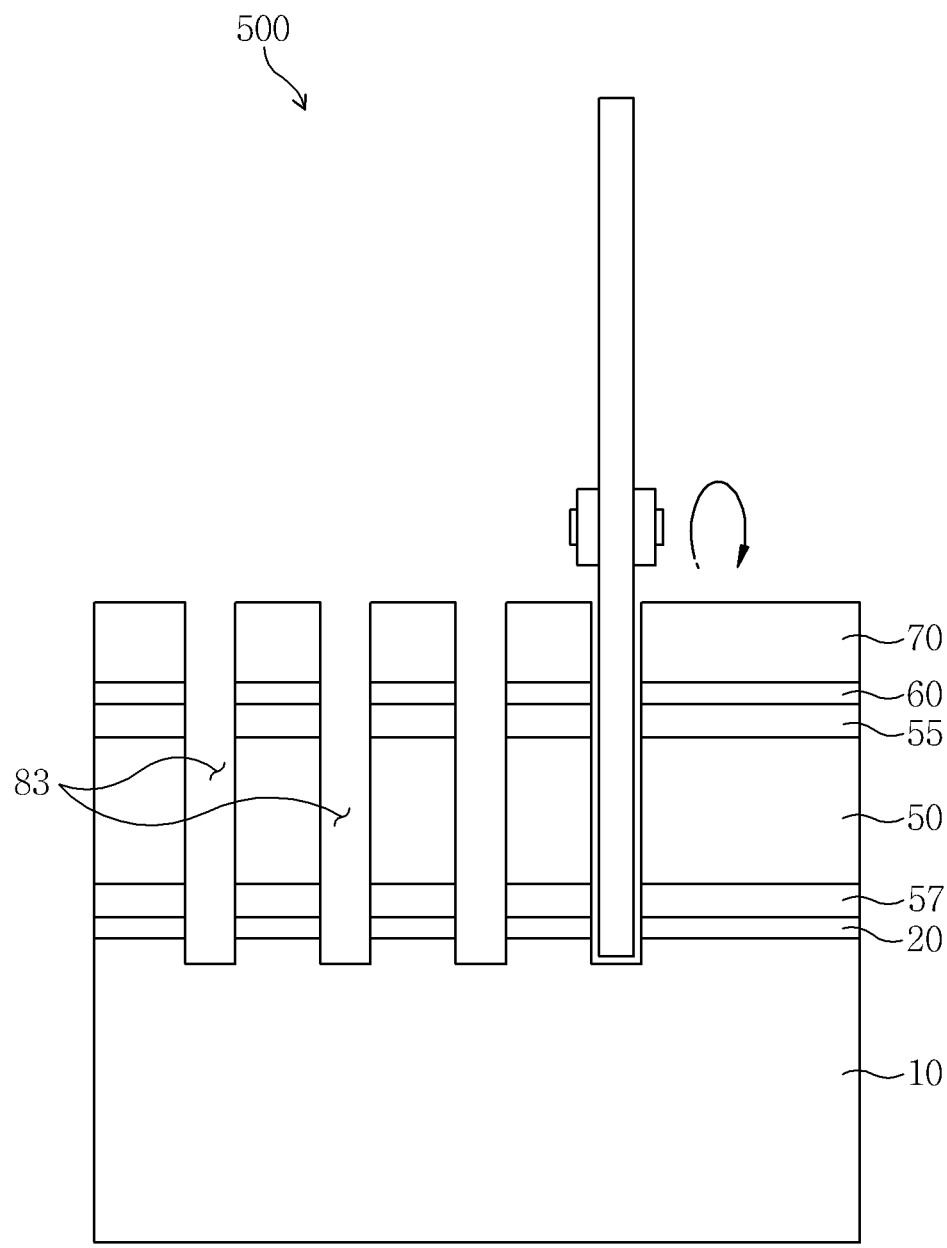
FIG. 6 illustrates a method of forming slots of the ultrasonic probe according to the first embodiment of the present invention.

A method of fabricating the ultrasonic probe according to the first embodiment of the present invention will now be explained with reference to FIGS. 2 through 6. FIG. 5 is a flowchart showing the method of fabricating the ultrasonic probe according to the first embodiment of the present invention and FIG. 6 illustrates a method of forming the slots of the ultrasonic probe according to the first embodiment of the present invention.

Referring to FIG. 5, the piezoelectric wafer 50, the ground electrode plate 60 and the acoustic matching layer 70 are sequentially stacked in step S711.

The plurality of first vertical holes 53 are formed in the piezoelectric wafer 50 in step S713.

The rear block 10 and the flexible printed circuit board 20 are sequentially stacked in step S715.

The piezoelectric wafer 50, stacked in step S711, is located on the top face of the flexible printed circuit board 20, stacked in step S715, in step S721.

When the rear block 10, the flexible printed circuit board 20, the piezoelectric wafer 50, the ground electrode plate 60 and the acoustic matching layer 70 are sequentially stacked, the plurality of slots 83 are formed such that the plurality of slots 83 range from the acoustic matching layer 70 to the top of the rear block 10 in the direction perpendicular to the first vertical holes 53 in step S723.

The acoustic lens (not shown) is bonded onto the acoustic matching layer 70 having the slots 83 formed therein to cover the overall surface of the acoustic matching layer 70 in step S725. The acoustic lens is formed of a material such as silicon and bonded onto the acoustic matching layer 70 using a silicon primer.

The ground electrode plate 60 is connected to the ground layer 59 of the flexible printed circuit board 20 and both ends of the flexible printed circuit board 20 are bonded to each other to connect the first and second wiring patterns 45 and 55 to construct a circuit in step S727.

The method of forming the slots 83 in step S723 will now be explained with reference to FIG. 6.

Referring to FIG. 6, the slots 83 are formed in the rear block 10, the flexible printed circuit board 20, the piezoelectric wafer 50, the ground electrode plate 60 and the acoustic matching layer 70, stacked in step 3723, using a dicing machine 500. FIG. 6 shows that four of five slots 83 are formed.

The dicing machine 500 used in step S723 can be used to form the first vertical holes 53 in the piezoelectric wafer 50.

The ultrasonic probe according to the present invention is bonded using general epoxy in the stacking and bonding steps because electrical bonding can be achieved by coating the general epoxy thin by 1 to 2.mu.m. While the general epoxy substitutes for a conductive epoxy having relatively weak adhesiveness, the adhesive used to bond the ultrasonic probe is not limited to the general epoxy.

Figure 7:
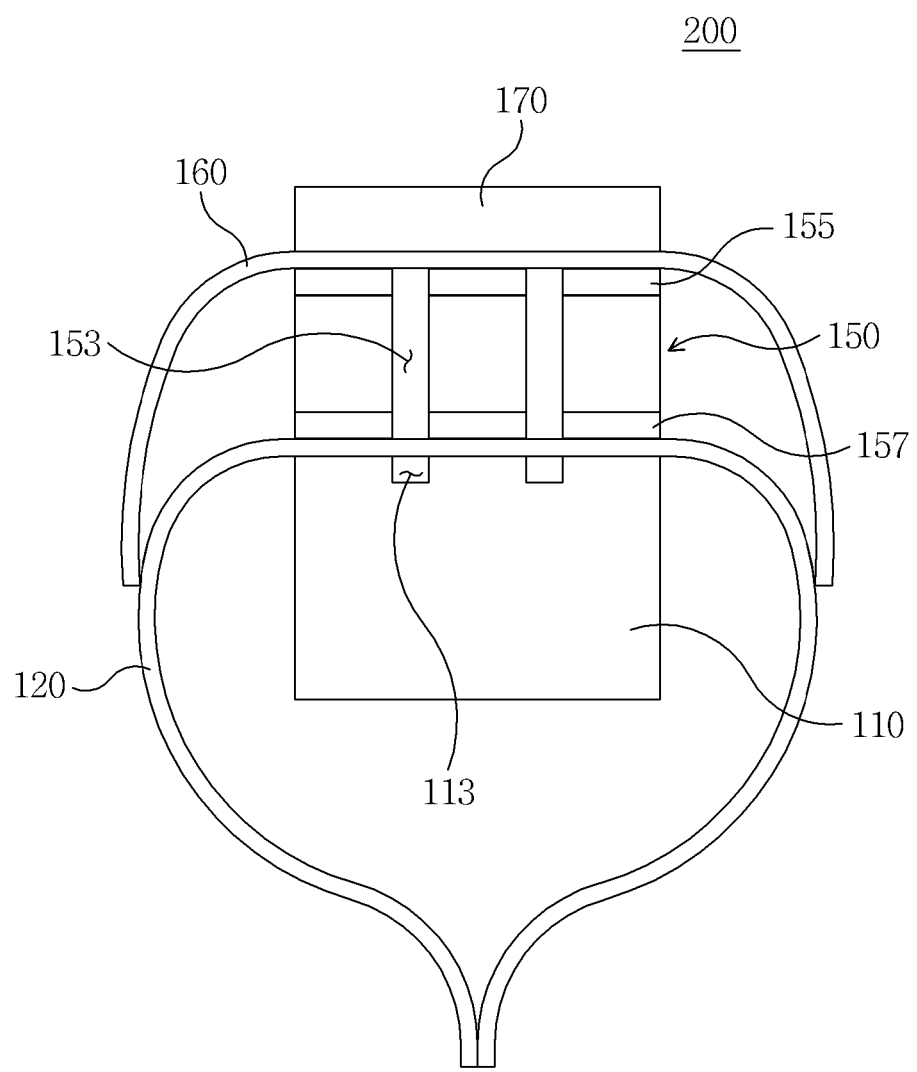
FIG. 7 is a cross-sectional view of an ultrasonic probe according to a second embodiment of the present invention.

An ultrasonic probe 200 according to a second embodiment of the present invention will now be explained with reference to FIGS. 7 and 8. FIG. 7 is a cross-sectional view of the ultrasonic probe 200 according to the second embodiment of the present invention and FIG. 8 is a flowchart showing a method of fabricating the ultrasonic probe 200 according to the second embodiment of the present invention.

The ultrasonic probe 200 according to the second embodiment of the present invention includes a plurality of second vertical holes 113 formed in a rear block 110 and a plurality of first vertical holes 153 formed in a piezoelectric wafer 150. The number of second vertical holes 113 equals the number of first vertical holes 113 and the second vertical and first vertical holes 113 and 153 have the same size. The ultrasonic probe 200 according to the second embodiment of the present invention can reduce ultrasonic interference and improve vibration property according to the second vertical holes 113 formed in the rear block 110.

Figure 8:
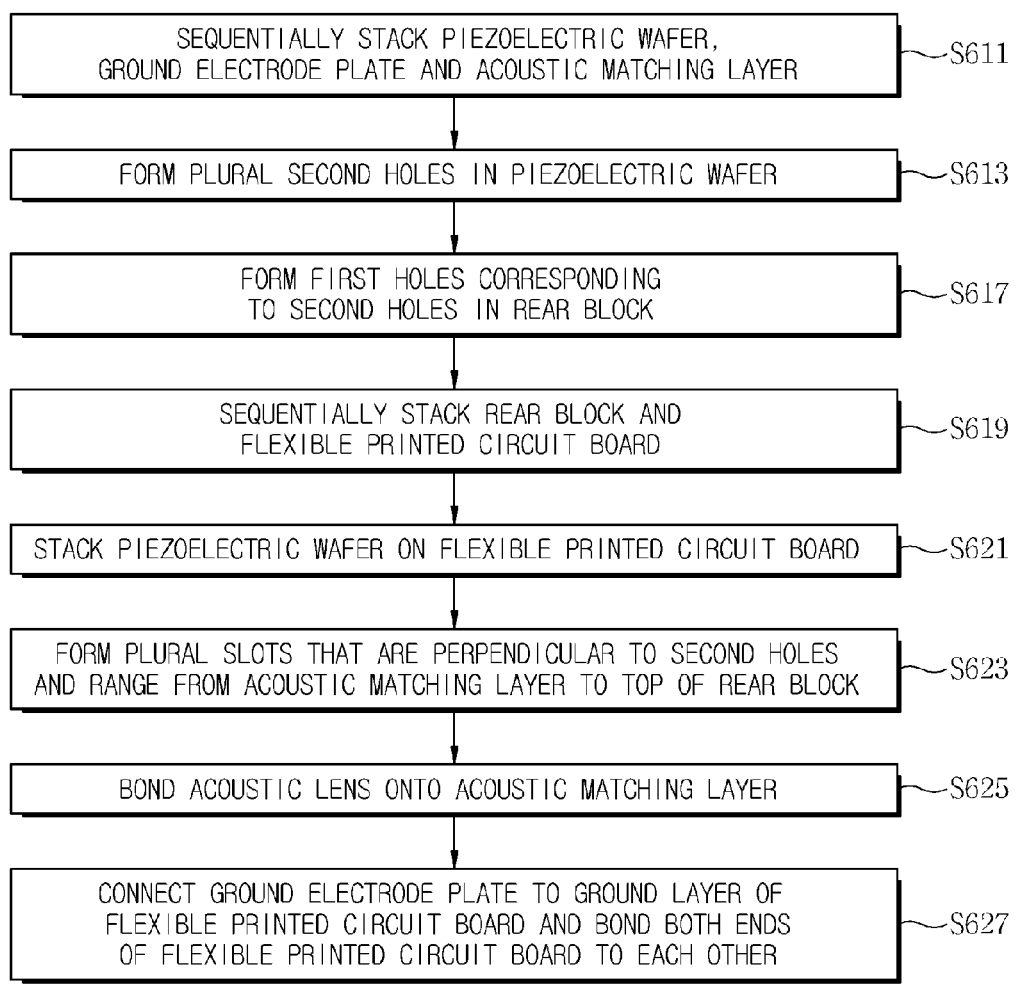
FIG. 8 is a flowchart showing a method of fabricating the ultrasonic probe according to the second embodiment of the present invention.

Referring to FIGS. 7 and 8, the piezoelectric wafer 150, a ground electrode plate 160 and an acoustic matching layer 170 are sequentially stacked in step S611. The plurality of first vertical holes 153 are formed in the piezoelectric wafer 150 in step S613 and the second vertical holes 113 corresponding to the first vertical holes 153 are formed in the rear block 110 in step S617.

The rear block 110 having the second vertical holes 113 formed therein and a flexible printed circuit board 120 are sequentially stacked in step S619. Here, it is more desirable to form the second vertical holes 113 in the rear block 110 and then stack the flexible printed circuit board 120 on the rear block 110.

The piezoelectric wafer 150, arranged in step S611, is stacked on the flexible printed circuit board 120, placed on the rear block 110 in step S619, in step S621.

A plurality of slots (not shown) perpendicular to the first vertical holes 153 are formed such that the slots range from the acoustic matching layer 170 to the top of the rear block 110 in step S623.

An acoustic lens (not shown) is bonded onto the acoustic matching layer 170 having the slots formed therein to cover the overall surface of the acoustic matching layer 170 in step S625.

The ground electrode plate 160 is connected to a ground layer (not shown) of the flexible printed circuit board 120 and both ends of the flexible printed circuit board 120 are bonded to each other to connect first and second wiring patterns (not shown) to thereby construct a circuit in step S627.

Figure 9:
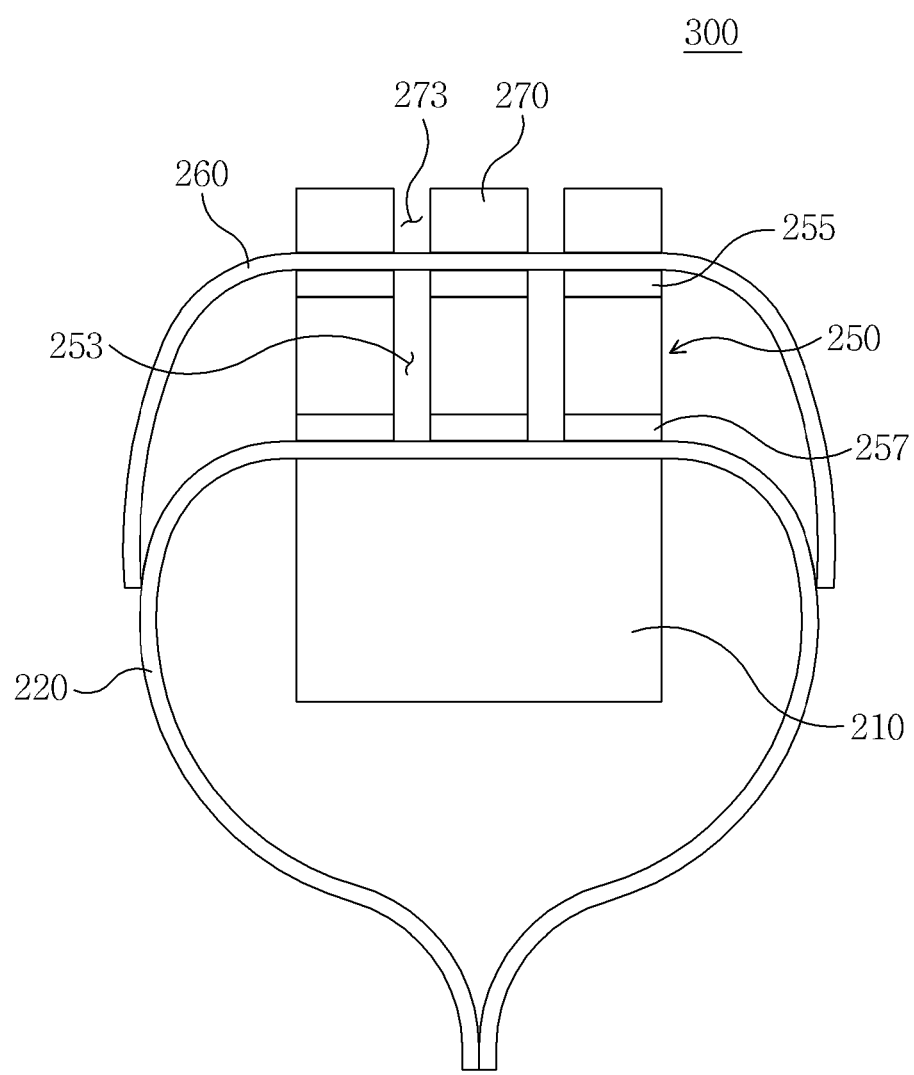
FIG. 9 is a cross-sectional view of an ultrasonic probe according to a third embodiment of the present invention.

An ultrasonic probe 200 according to a third embodiment of the present invention will now be explained with reference to FIGS. 9 and 10. FIG. 9 is a cross-sectional view of the ultrasonic probe 300 according to the third embodiment of the present invention and FIG. 10 is a flowchart showing a method of fabricating the ultrasonic probe 300 according to the third embodiment of the present invention.

The ultrasonic probe 300 according to the third embodiment of the present invention includes a plurality of first vertical holes 253 formed in a piezoelectric wafer 250 and a plurality of third vertical holes 273 formed in an acoustic matching layer 270. Here, the number of first vertical holes 273 equals the number of third vertical holes 273 and the first vertical and third vertical holes 253 and 273 have the same size. The ultrasonic probe 300 according to the third embodiment of the present invention reduces ultrasonic interference according to the third vertical holes 273 formed in the acoustic matching layer 270 to improve vibration property.

Figure 10:
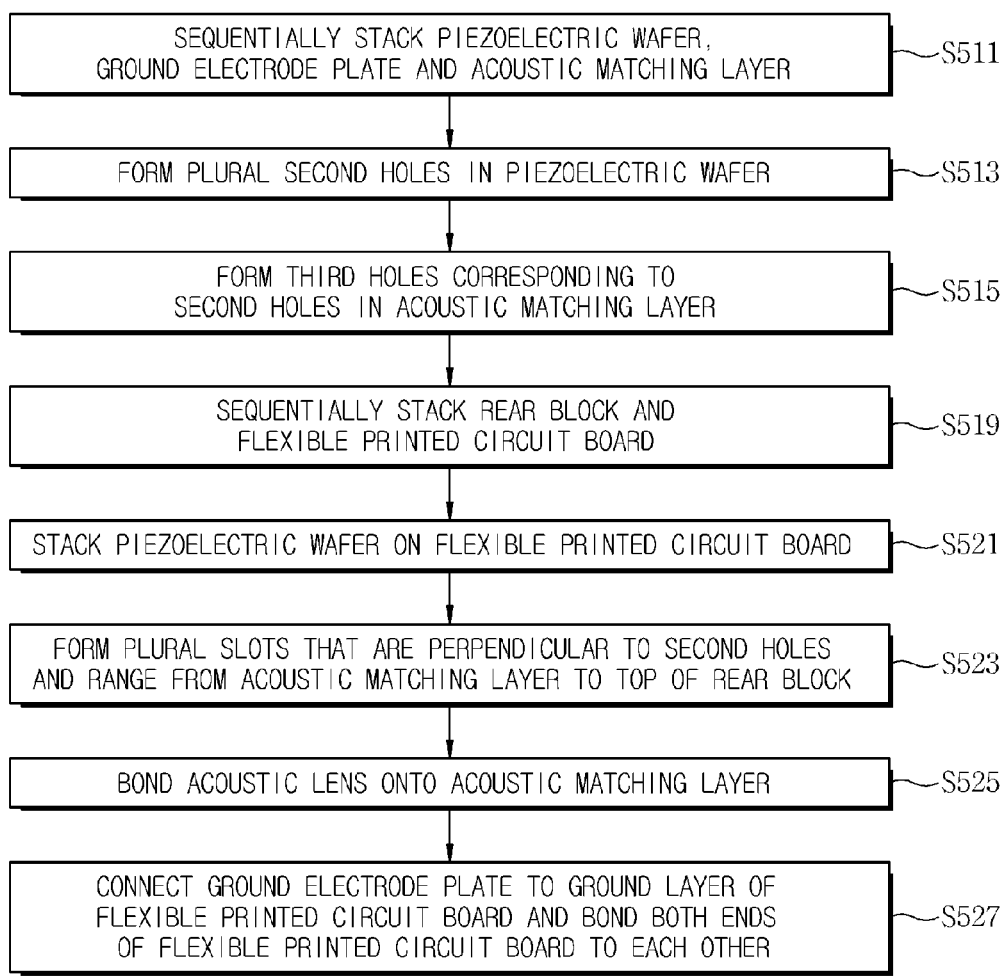
FIG. 10 is a flowchart showing a method of fabricating the ultrasonic probe according to the third embodiment of the present invention.

Referring to FIGS. 9 and 10, the piezoelectric wafer 250, a ground electrode plate 260 and an acoustic matching layer 270 are sequentially stacked in step S511. The plurality of first vertical holes 253 are formed in the piezoelectric wafer 250 in step S513 and the third vertical holes 273 corresponding to the first vertical holes 253 are formed in the acoustic matching layer 270 in step S515.

A rear block 210 and a flexible printed circuit board 220 are sequentially stacked in step S519.

The piezoelectric wafer 250, arranged in step S511, is stacked on the flexible printed circuit board 220, placed on the rear block 210 in step S519, in step S521.

A plurality of slots (not shown) perpendicular to the first vertical holes 253 are formed such that the slots range from the acoustic matching layer 270 to the top of the rear block 210 in step S523.

An acoustic lens (not shown) is bonded onto the acoustic matching layer 270 having the slots formed therein to cover the overall surface of the acoustic matching layer 270 in step S525.

The ground electrode plate 260 is connected to a ground layer (not shown) of the flexible printed circuit board 220 and both ends of the flexible printed circuit board 220 are bonded to each other to connect first and second wiring patterns (not shown) to thereby construct a circuit in step S527.

Figure 11A:
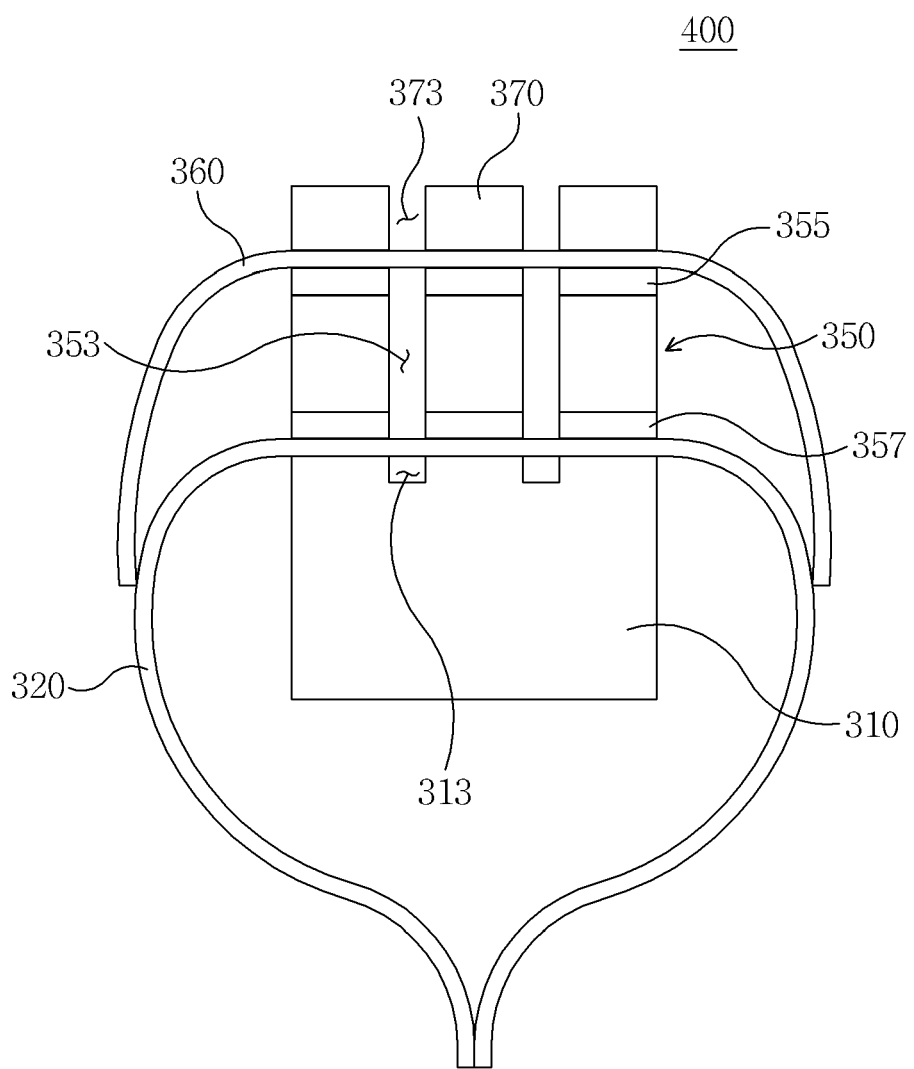
FIG. 11A is a cross-sectional view of an ultrasonic probe according to a fourth embodiment of the present invention.

An ultrasonic probe 400 according to a fourth embodiment of the present invention will now be explained with reference to FIGS. 11A, 11B and 12. FIG. 11A is a cross-sectional view of the ultrasonic probe 400 according to the fourth embodiment of the present invention, FIG. 11B is a perspective view of the ultrasonic probe 400 according to the fourth embodiment of the present invention and FIG. 12 is a flowchart showing a method of fabricating the ultrasonic probe 400 according to the fourth embodiment of the present invention.

The ultrasonic probe 400 according to the fourth embodiment of the present invention includes a plurality of second vertical holes 313 formed in a rear block 310, a plurality of first vertical holes 353 formed in a piezoelectric wafer 350 and a plurality of third vertical holes 373 formed in an acoustic matching layer 370. The number of second vertical holes 313, the number of first vertical holes 353 and the number of third vertical holes 373 are identical and the first, first vertical and third vertical holes 313, 353 and 373 have the same size. The ultrasonic probe 400 according to the fourth embodiment of the present invention can minimize inter-layer interference according to the first, first vertical and third vertical holes 313, 353 and 373 formed in the rear block 310, the piezoelectric wafer 350 and the acoustic matching layer 370 to improve vibration property.

Figure 11B:
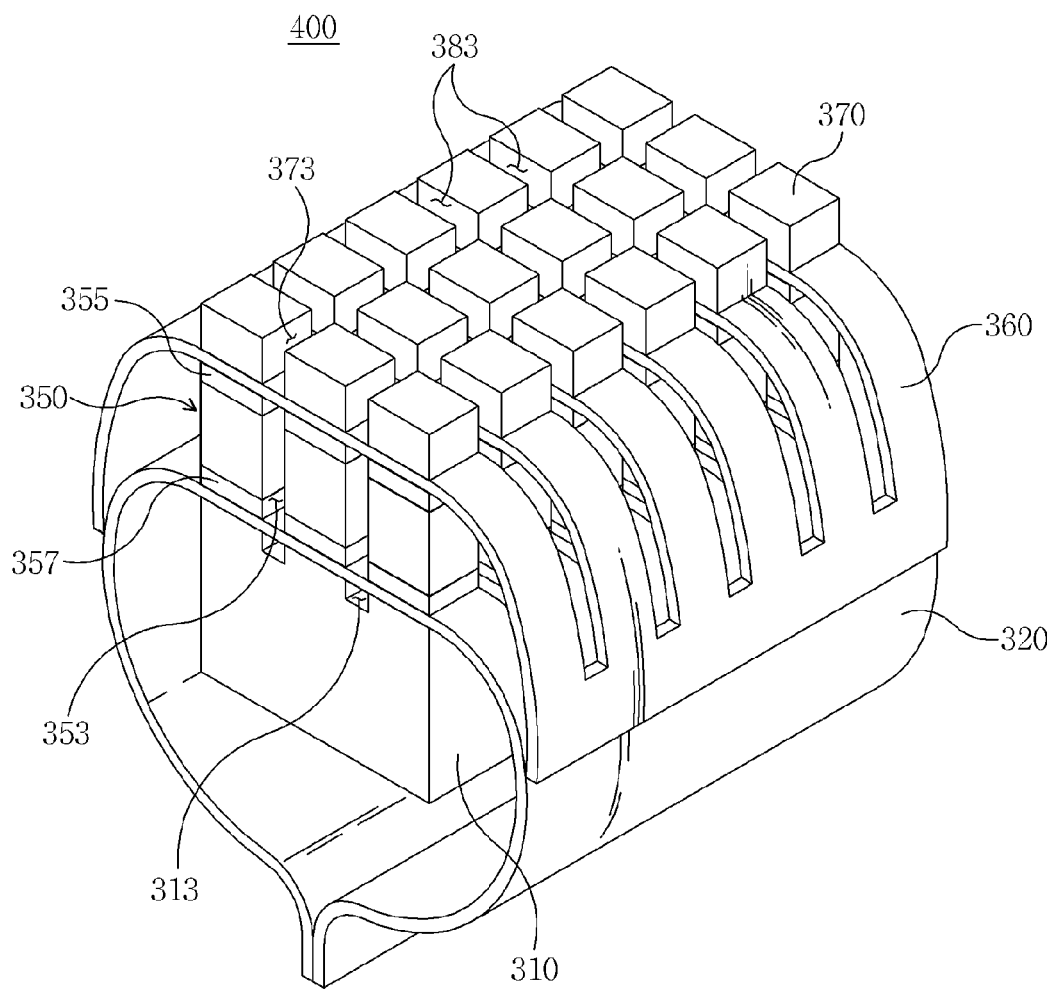
FIG. 11B is a perspective view of the ultrasonic probe according to the fourth embodiment of the present invention.
Figure 12:
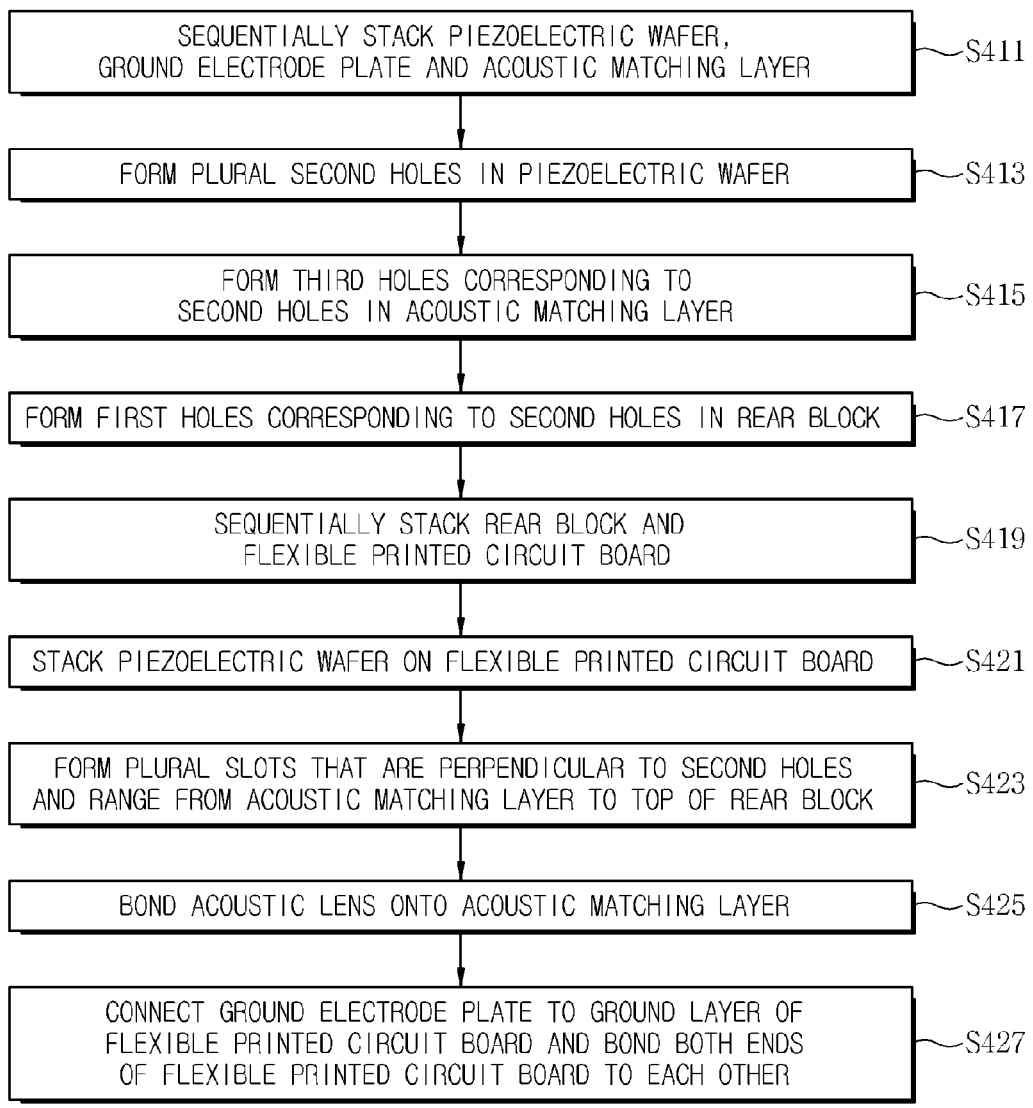
FIG. 12 is a flowchart showing a method of fabricating the ultrasonic probe according to the fourth embodiment of the present invention.

Referring to FIGS. 11A, 11B and 12, the piezoelectric wafer 350, a ground electrode plate 360 and the acoustic matching layer 370 are sequentially stacked in step S411. The plurality of first vertical holes 353 are formed in the piezoelectric wafer 350 in step S413 and the third vertical holes 373 corresponding to the first vertical holes 353 are formed in the acoustic matching layer 370 in step S415. The second vertical holes 313 corresponding to the first vertical and third vertical holes 353 and 373 are formed in the upper part of the rear block 310 in step S417.

The rear block 310 having the second vertical holes 313 formed therein and a flexible printed circuit board 320 are sequentially stacked in step S419.

The piezoelectric wafer 350, arranged in step S411, is stacked on the flexible printed circuit board 320, placed on the rear block 310 in step S419, in step S421.

When the rear block 310, the flexible printed circuit board 320, the piezoelectric wafer 350, the ground electrode plate 360 and the acoustic matching layer 370 are sequentially stacked in step S421, a plurality of slots 383 perpendicular to the first vertical holes 353 are formed such that the slots 383 range from the acoustic matching layer 370 to the top of the rear block 310 in step S423.

An acoustic lens (not shown) is bonded onto the acoustic matching layer 370 having the slots 383 formed therein to cover the overall surface of the acoustic matching layer 370 in step S425.

The ground electrode plate 360 is connected to a ground layer 359 of the flexible printed circuit board 320 and both ends of the flexible printed circuit board 320 are bonded to each other to connect first and second wiring patterns (not shown) to thereby construct a circuit in step S427.

The ultrasonic probe, the ultrasonic imaging apparatus and the fabricating method thereof according to the present invention have been described through embodiments. While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. An ultrasonic probe comprising:
a rear block having a predetermined thickness;
a flexible printed circuit board stacked on the rear block to surround the top face and side of the rear block and having wiring patterns formed thereon;
a piezoelectric wafer stacked on the top face of the flexible printed circuit board and having upper and lower electrodes respectively formed on top and bottom faces thereof;
a ground electrode plate stacked on the top face of the piezoelectric wafer, bonded to the upper electrode and connected to a ground layer of the flexible printed circuit board;
an acoustic matching layer stacked on the top face of the ground electrode plate; and
an acoustic lens bonded onto the acoustic matching layer;
wherein the piezoelectric wafer has first vertical holes elongated in one horizontal direction,
wherein vertical slots are formed in the acoustic matching layer, the ground electrode plate, the piezoelectric wafer and the flexible printed circuit board, and are elongated in another horizontal direction perpendicular to the one horizontal direction,
wherein the flexible printed circuit board comprises:
a base film formed of an insulating material and having a bottom face bonded onto the rear block and a top face opposite to the bottom face; and
wiring patterns formed on both faces of the base film, wherein the wiring patterns comprises:
a central wiring pattern that is formed on the top face of the base film, has a central pad formed between neighboring first vertical holes, and is extended to the bottom face of the base film through a via;
a first wiring pattern that has a first pad formed adjacent to one side of the central pad, and is extended to one side of the top face of the base film;
a second wiring pattern that has a second pad formed adjacent to the opposite side of the central pad, and is extended to the opposite side of the top face of the base film;
a protective layer formed on the top face of the base film so as to cover the first and second wiring patterns except the first and second pads, and formed on the bottom face of the base film so as to cover the central wiring pattern except the central pad; and
a ground layer formed on the protective layer formed on the top face of the base film, and connected to the ground electrode plate.

2. The ultrasonic probe of claim 1, wherein the rear block has second vertical holes formed therein, the second vertical holes being vertically extended from the first vertical holes.

3. The ultrasonic probe of claim 1, wherein the acoustic matching layer has third vertical holes formed therein, the third vertical holes being vertically extended from the first vertical holes.

4. The ultrasonic probe of claim 1, wherein the rear block has second vertical holes formed therein, the second vertical holes being vertically extended from the first vertical holes, and the acoustic matching layer has third vertical holes formed therein, the third vertical holes being vertically extended from the first vertical holes.

5. The ultrasonic probe of claim 4, wherein the first, second and third holes have the same size.

6. The ultrasonic probe of claim 5, wherein the number of first holes, the number of second holes and the number of third holes are two or four.

7. The ultrasonic probe of claim 1, wherein the central wiring pattern is alternately arranged on one side and the other side of the base film.

8. The ultrasonic probe of claim 7, wherein both ends of the flexible printed circuit board are bonded to each other such that the first and second wiring patterns are connected to each other.

9. The ultrasonic probe of claim 8, wherein the central pad, the first pad and the second pad form a 3×96 matrix array.

10. The ultrasonic probe of claim 9, wherein the number of slots is 95.

11. An ultrasonic imaging apparatus comprising:
the ultrasonic probe according to claim 1; and
a main body having a connector connected to the ultrasonic probe.

12. The ultrasonic imaging apparatus of claim 11, wherein the connector is located on the top of the main body.

* * * * *